(12) United States Patent
Beroza

(10) Patent No.: US 7,913,449 B2
(45) Date of Patent: Mar. 29, 2011

(54) DEVICE FOR EXTENDING DURATION OF VOLATILE LIQUID LURES

(75) Inventor: Morton Beroza, Silver Spring, MD (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 1068 days.

(21) Appl. No.: 10/247,739

(22) Filed: Sep. 20, 2002

(65) Prior Publication Data

US 2004/0055207 A1 Mar. 25, 2004

(51) Int. Cl.
*A01M 1/02* (2006.01)
*A01M 1/20* (2006.01)
(52) U.S. Cl. .............. 43/131; 43/107; 43/122; 43/132.1
(58) Field of Classification Search .................... 43/107, 43/122, 124, 131, 132.1
See application file for complete search history.

(56) References Cited

U.S. PATENT DOCUMENTS

| | | | | | |
|---|---|---|---|---|---|
| 1,056,535 | A | * | 3/1913 | Grimes et al. | 43/131 |
| 1,924,379 | A | * | 8/1933 | Reese | 43/122 |
| 2,254,948 | A | * | 9/1941 | Kubalek | 43/131 |
| 2,573,972 | A | * | 10/1951 | Reinhardt | 239/47 |
| 4,310,985 | A | * | 1/1982 | Foster et al. | 43/131 |
| 4,662,103 | A | * | 5/1987 | Cheng | 43/131 |
| 4,745,705 | A | * | 5/1988 | Yamamoto et al. | 43/125 |
| 4,802,303 | A | * | 2/1989 | Floyd, III | 43/131 |
| 4,908,977 | A | * | 3/1990 | Foster | 43/107 |
| 5,018,299 | A | * | 5/1991 | Peek et al. | 43/107 |
| 5,501,033 | A | * | 3/1996 | Wefler | 43/131 |
| 5,647,164 | A | * | 7/1997 | Yates | 43/139 |
| 6,209,252 | B1 | * | 4/2001 | McGough | 43/1 |
| 6,223,465 | B1 | * | 5/2001 | Soller et al. | 43/131 |
| 6,482,365 | B1 | * | 11/2002 | Soller | 422/126 |
| 6,530,172 | B2 | * | 3/2003 | Lenz | 43/112 |
| 6,532,695 | B1 | * | 3/2003 | Alvarado | 43/122 |
| 6,543,181 | B1 | * | 4/2003 | Baker et al. | 43/107 |
| 6,585,990 | B1 | * | 7/2003 | Huang | 424/405 |
| 2003/0061757 | A1 | * | 4/2003 | Askin | 43/112 |

FOREIGN PATENT DOCUMENTS

JP 4-179426 * 6/1992

* cited by examiner

*Primary Examiner* — David J Parsley
(74) *Attorney, Agent, or Firm* — John D. Fado; Gail E. Poulos

(57) ABSTRACT

A liquid-lure dispenser that provides long-time uniform emission of an attractant that entices insects or other organisms into a trap, consists of a wick that absorbs the liquid lure from its container and gradually emits the lure to the atmosphere from the exposed portion of the wick. The tubular container holds the desired quantity of lure and has an opening that holds the wick securely in place, with the lower part of the wick immersed in lure and the upper part exposed to air; lure-emission rate can be adjusted by area of wick exposed to air. An opening in the lure container permits lure to be added as needed and avoids an air-pressure drop in the lure container as lure is sucked up by the wick and volatilized. If desirable, insecticide or more than one lure may be released from a dispenser.

5 Claims, 1 Drawing Sheet

DEVICE FOR EXTENDING DURATION OF VOLATILE LIQUID LURES

This invention was sponsored by the United States Department of Agriculture Agreement Number 58-0790-2-154.

BACKGROUND OF THE INVENTION

1. Field of the Invention

This invention relates to a device that will provide a uniform emission rate of a lure providing maximum attraction for flying insects for an extended period of time.

2. Description of the Related Art

Such lures are currently employed to detect and monitor for the presence of insect and other species that respond to lure-baited traps; e.g., the Mediterranean fruit fly (or medfly), melon fly, codling moth, mosquitoes, etc.

The information derived is used to determine where and when control measures—such as insecticide applications, sterile-insect release, mass trapping—are to be applied. The operation makes for a very efficient means of controlling or eradicating the targeted species from infested areas (especially large ones), and therefore is highly desirable from an agricultural and ecological standpoint. If pesticide is to be used, the procedure allows it to be applied only were needed and only as long as needed to effect control or eradication of the targeted species. Thus, the environment becomes less contaminated, and money is saved because less insecticide is used. Also noteworthy, the lure-baited traps have enabled eradication of such insect pests as the medfly, gypsy moth, boll weevil, melon fly from extensive areas of the United States.

Currently such traps, e.g., for the medfly, are manually examined every 2 to 3 weeks for medflies and for rebaiting of the lure, However, a new detection procedure has been advanced to replace the current one (patent application Ser. No. 10/097,629). With this procedure, the need for manual inspection of traps for detection of targeted insects can be extended to at least several months. However, a means that would likewise extend (without rebaiting of the lure) the uniform emission of the lure for a much longer period—e.g., for 2 or 3 month—was likewise needed. The lure dispenser described below has been devised to accomplish this task.

DETAILED DESCRIPTION OF THE INVENTION

Obviously a variety of shapes of the container, wire, and wick opening would work well without departing from the basic ideas presented here. Thus, one could use a small bottle of appropriate size and shape to hold the desired amount of liquid and an appropriate opening to hold the wick partly immersed in lure and partly exposed to air. The wick opening can be square, or oblong to accommodate a flat dispenser; or the wick can be somewhat loose to allow air to enter the lure container (C) around the wick. Also, having the lure container horizontal (to change the lure level as little as possible as it is volatilized) will allow lure emission to be more uniform than if the container were a deep vertical one.

The wire-hanging arrangement of the lure dispenser from the trap top is most convenient. Removal and replacement of the dispenser from the Delta trap (See next paragraph) is easily done. With some traps, it may be more convenient to place the dispenser elsewhere in the trap; for example, on the bottom, without departing from the basic concepts being advanced.

Figure 1:
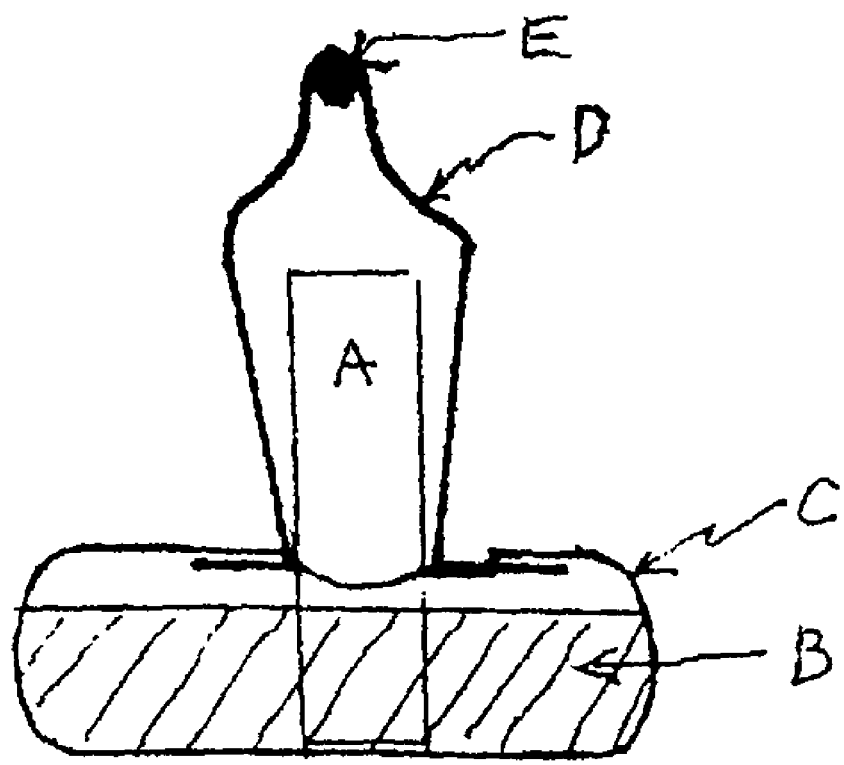
FIG. 1 is a side-view of the lure dispenser being advanced to provide extended uniform emission of an attractant that lures insects or other organisms into a trap. The wick (A) can be an ordinary cylindrical cotton wick (or other porous inert medium) that will absorb the liquid lure (B) from its container (C) and gradually emit the lure from the exposed portion of the wick to the atmosphere. The container (c), made of glass or other inert material, which holds the desired quantity of lure, has a circular opening that holds the cylindrical wick securely in place. The lower part of the wick is immersed in the lure, and the upper part of the wick is exposed to the atmosphere. Rate of emission of lure can be regulated by the area of wick exposed to air. The wire (D) hold the container (C) upright as it hangs from the anchor (E) located at the top of the trap.
Figure 2:
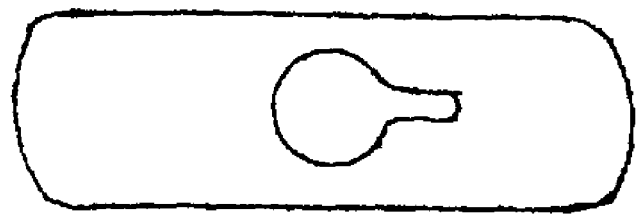
FIG. 2 is a top-view of the lure container (B) itself. Alongside the circular opening for the wick is a short connecting opening to allow air to enter the container (C). Without air available in the container (C), the air-pressure in (C) would decrease as lure is sucked up by the wick and evaporates; as a result, the drop in air pressure would decrease lure-emission rate, which is unacceptable. The container is held by the wire (D) placed in the hole holding the wick.
Figure 3:
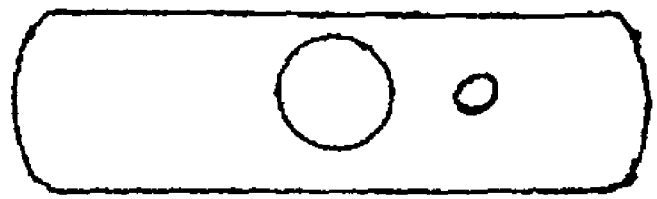
FIG. 3 is an equally effective container; it simply has a hole to allow air to enter the container (C) as the lure evaporates. The air opening in the container also serves to add additional lure as needed. The container is held by the wire (D) placed in the hole.

In tests conducted with trimedlure, the lure dispenser—shown in FIG. 1—was placed in the Delta trap currently used by the USDA in California. In another Delta trap, the lure (MAGNET TRIMEDLURE, 70-0 Plug, 2 g active) used by USDA in California was placed (and replaced biweekly). (The inside surface of the Delta trap is coated with a sticky substance, which traps insects responding to the lure). The loss of trimedlure from each trap was determined every few days by weighing the lure dispensers. Losses of trimedlure from the two dispensers were consistently about the same for an extended period of time. Although loss of trimedlure depended on the temperature, what was important was that the losses of trimedlure from the two different dispensers (exposed under identical conditions) were consistently similar.

The extended-lure dispenser should be especially useful in mass trapping for insect control. When infestations are found, traps with the extended-lure dispensers can be deployed in the infested areas without the need to replenish the lure for the extended period of time. Further, when inspecting the lure dispenser, the need to replenish the lure is readily visible, especially if the lure is colored.

When problems with the foregoing arrangements are encountered, variations of the procedure may be used. The container may be constructed to allow more or less of the wick exposed to obtain the desired uniform emission rate of lure to provide maximum attraction for flying insects. The container may be constructed larger or smaller to hold more or less of liquid lure (or insecticide). An inert liquid, with a volatility about equal to that of the lure, may be added to the lure to reduce rate of lure evaporation. A solid but volatile lure (or insecticide) may be dissolved in a liquid carrier to allow its use in the lure dispenser. More than one dispenser, e.g., for different insects, may be used in a trap, or more than one lure may be used in a single dispenser, provided the lures do not interfere appreciably with each other's attraction.

Finally, while it may be desirable to replace the wick periodically, the device itself can be used indefinitely; i.e., it does not deteriorate, and it can be used repeatedly. With a different lure, the device can be washed and then reloaded with a new lure.

What I claim as my invention is:

1. A lure-emitting device consisting of an extended uniform lure emission dispenser consisting of at least one volatile liquid lure specific for one targeted flying insect species an adjustable wick wherein said wick area exposed to the atmosphere can be increased or decreased over time to maintain a uniform rate of lure emission providing maximum attraction for said flying insect, and a means for maintaining air pressure in said dispenser wherein said dispenser emits said at least one volatile lure for at least about six months without replenishment of said lure.

2. The device of claim 1 wherein said means for maintaining air pressure is an opening in a top surface of said dispenser.

3. The device of claim 1 further consisting of at least one insecticide.

4. A trapping system consisting of at least one open-ended trap that allows air passage through said trap comprising an extended uniform lure emission dispenser consisting of at least one volatile liquid lure specific for one targeted flying insect species, an adjustable wick for providing a uniform rate of emission of said lure wherein said wick area exposed to the atmosphere can be increased or decreased over time to maintain a uniform lure emission rate providing maximum flying insect attraction, and a means for maintaining air pressure in said dispenser, wherein said dispenser provides a uniform rate of lure emission for at least about six months without replenishment of said lure.

5. A method for providing extended uniform lure emission for attracting specific flying insect species to a trap consisting of:
   (a) providing a volatile lure-containing dispenser consisting of an adjustable wick and a means for maintaining air pressure in said dispenser,
   (b) adjusting said wick by raising and lowering said wick in order to maintain maximum uniform lure emission,
   (c) placing said dispenser in a trap, and
   (d) placing lure-containing traps in areas where targeted flying-insect capture is desired wherein said dispenser uniformly emits lure for at least six months without replenishment of said lure.

* * * * *